(12) United States Patent
Shida (10) Patent No.: US 9,313,388 B2
(45) Date of Patent: Apr. 12, 2016

(54) FLUORESCENCE OBSERVATION DEVICE (71) Applicant: OLYMPUS CORPORATION, Tokyo (JP)

(72) Inventor: Hiromi Shida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 163 days.

(21) Appl. No.: 13/869,210

(22) Filed: Apr. 24, 2013

(65) Prior Publication Data

US 2013/0235258 A1 Sep. 12, 2013

Related U.S. Application Data

(63) Continuation of application No. PCT/JP2011/074058, filed on Oct. 19, 2011.

(30) Foreign Application Priority Data

Oct. 28, 2010 (JP) ................................ 2010-242608

(51) Int. Cl.
*H04N 5/222* (2006.01)
*H04N 13/00* (2006.01)
(Continued)

(52) U.S. Cl.
CPC .......... *H04N 5/2256* (2013.01); *A61B 1/00009* (2013.01); *A61B 1/00186* (2013.01); *A61B 1/043* (2013.01); *A61B 1/05* (2013.01); *A61B 1/0669* (2013.01); *A61B 1/0646* (2013.01)

(58) Field of Classification Search
CPC ........... A61B 1/00009; A61B 1/00096; A61B 1/043; A61B 1/0638; A61B 1/0646; G03B 21/16; G03B 21/2033; H04N 21/41407; H04N 21/4318; H04N 21/44008; H04N 5/20; H04N 5/58; H04N 7/0122; H04N 9/312
USPC ................... 348/45, 70, 229.1, 370; 382/151; 600/476
See application file for complete search history.

(56) References Cited

U.S. PATENT DOCUMENTS 4,768,513 A 9/1988 Suzuki
5,749,830 A 5/1998 Kaneko et al.
(Continued)

FOREIGN PATENT DOCUMENTS

EP 1 256 310 A2 11/2002
JP 62-247232 A 10/1987
(Continued)

OTHER PUBLICATIONS

Extended Supplementary European Search Report dated Oct. 22, 2013 from related European Application No. 11 83 6106.2.
(Continued)

*Primary Examiner* — Trung Diep
(74) *Attorney, Agent, or Firm* — Scully, Scott, Murphy & Presser, P.C.

(57) ABSTRACT

Provided is a fluorescence observation device comprising an illuminating section that emits excitation light and illumination light onto a subject; a fluorescence-image capturing section that acquires a fluorescence image by image-capturing fluorescence generated in the subject by irradiation with the excitation light from the illuminating section; a return-light-image capturing section that acquires a return-light image by image-capturing return light that returns from the subject by irradiation with the illumination light from the illuminating section; a region extracting section that extracts a high-luminance region in which the fluorescence image acquired by the fluorescence-image capturing section has a gradation level higher than or equal to a set threshold value; and a threshold setting section that sets the threshold value higher as the gradation level of the return-light image acquired by the return-light-image capturing section increases.

12 Claims, 6 Drawing Sheets

(51) Int. Cl.
  *H04N 5/225* (2006.01)
  *A61B 1/00* (2006.01)
  *A61B 1/04* (2006.01)
  *A61B 1/05* (2006.01)
  *A61B 1/06* (2006.01)

(56) References Cited

U.S. PATENT DOCUMENTS

| | | | |
|---|---|---|---|
| 7,636,464 B2* | 12/2009 | Kobayashi | A61B 1/043 348/70 |
| 2002/0177780 A1 | 11/2002 | Sendai | |
| 2006/0025692 A1 | 2/2006 | Ishihara | |
| 2006/0058684 A1 | 3/2006 | Sendai | |
| 2006/0262211 A1* | 11/2006 | Kido | 348/308 |
| 2009/0147998 A1* | 6/2009 | Yamaguchi et al. | 382/106 |
| 2009/0322863 A1 | 12/2009 | Takahashi | |
| 2010/0049058 A1 | 2/2010 | Ishihara | |
| 2010/0245551 A1 | 9/2010 | Morita | |
| 2010/0245552 A1 | 9/2010 | Higuchi | |

FOREIGN PATENT DOCUMENTS

| | | |
|---|---|---|
| JP | 2001-204683 A | 7/2001 |
| JP | 2002-28125 A | 1/2002 |
| JP | 2002-119463 A | 4/2002 |
| JP | 2003-24268 A | 1/2003 |
| JP | 2003-290130 A | 10/2003 |
| JP | 2006-61435 A | 3/2006 |
| JP | 2006-61683 A | 3/2006 |
| JP | 2006-191989 A | 7/2006 |
| JP | 2006-314581 A | 11/2006 |
| JP | 2008-154846 A | 7/2008 |
| JP | 2010-5095 A | 1/2010 |
| JP | 2010-200883 A | 9/2010 |
| JP | 2010-227256 A | 10/2010 |

OTHER PUBLICATIONS

International Search Report dated Nov. 29, 2011 issued in PCT/JP2011/074058.

* cited by examiner

FLUORESCENCE OBSERVATION DEVICE

CROSS-REFERENCE TO RELATED APPLICATIONS

This is a continuation of International Application PCT/JP2011/074058, with an international filing date of Oct. 19, 2011, which is hereby incorporated by reference herein in its entirety. This application claims the benefit of Japanese Patent Application No. 2010-242608, the contents of which are incorporated herein by reference.

TECHNICAL FIELD

The present invention relates to a fluorescence observation device.

BACKGROUND ART

A known fluorescence observation device in the related art acquires a reflected-light image and a fluorescence image of an observation target and detects also a region having low fluorescence intensity in the fluorescence image as a lesion depending on whether the signal strength of the reflected-light image exceeds a predetermined set level (for example, see PTL 1).

CITATION LIST

Patent Literature

{PTL 1} Japanese Unexamined Patent Application, Publication No. 2006-191989

SUMMARY OF INVENTION

An aspect of the present invention provides a fluorescence observation device comprising an illuminating section that emits excitation light and illumination light onto a subject; a fluorescence-image capturing section that acquires a fluorescence image by image-capturing fluorescence generated in the subject by irradiation with the excitation light from the illuminating section; a return-light-image capturing section that acquires a return-light image by image-capturing return light that returns from the subject by irradiation with the illumination light from the illuminating section; a region extracting section that extracts a high-luminance region in which the fluorescence image acquired by the fluorescence-image capturing section has a gradation level higher than or equal to a set threshold value; and a threshold setting section that sets the threshold value higher as the gradation level of the return-light image acquired by the return-light-image capturing section increases.

In an aspect of the present invention, between a first gradation level and a second gradation level, the threshold setting section may set, according to a function, a threshold value that increases as the gradation level of the return-light image increases and, in a gradation level range lower than the first gradation level and in a gradation level range higher than the second gradation level, may set a threshold value larger than a value calculated using the function.

In an aspect of the present invention, the threshold setting section may be configured to set the threshold value for each of separated regions formed by separating the return-light image at intervals of a plurality of pixels; and the region extracting section may be configured to extract the high-luminance region for individual small regions of the fluorescence image located at positions corresponding to the respective separated regions by using the threshold value set for each of the separated regions.

The above configuration may further include an image separating section that separates the return-light image at intervals of a plurality of pixels to form the separated regions and that associates the small regions of the fluorescence image located at positions corresponding to the respective separated regions with the individual separated regions; and an average-gradation-level calculating section that calculates an average gradation level of a plurality of pixels in the return-light image, wherein the image separating section may increase the number of separations as the average gradation level calculated by the average-gradation-level calculating section increases.

In an aspect of the present invention, a detachable component that is attached and detached for changing observation conditions may be provided, wherein identification information may be stored in the detachable component, and an identification-information reading section that reads the identification information stored in the detachable component, a storage section that stores the identification information, the gradation level of the return-light image, and the threshold value in association with one another, and the threshold setting section that sets the threshold value stored in association by the storage section may be provided.

An example of the detachable component is a scope of an endoscope apparatus, and examples of observation conditions that have changed in this case include the wavelength and intensity of observable fluorescence and observation target sites (stomach, colon, etc.).

DESCRIPTION OF EMBODIMENTS

A fluorescence observation device according to a first embodiment of the present invention will be described with reference to the drawings.

Figure 1:
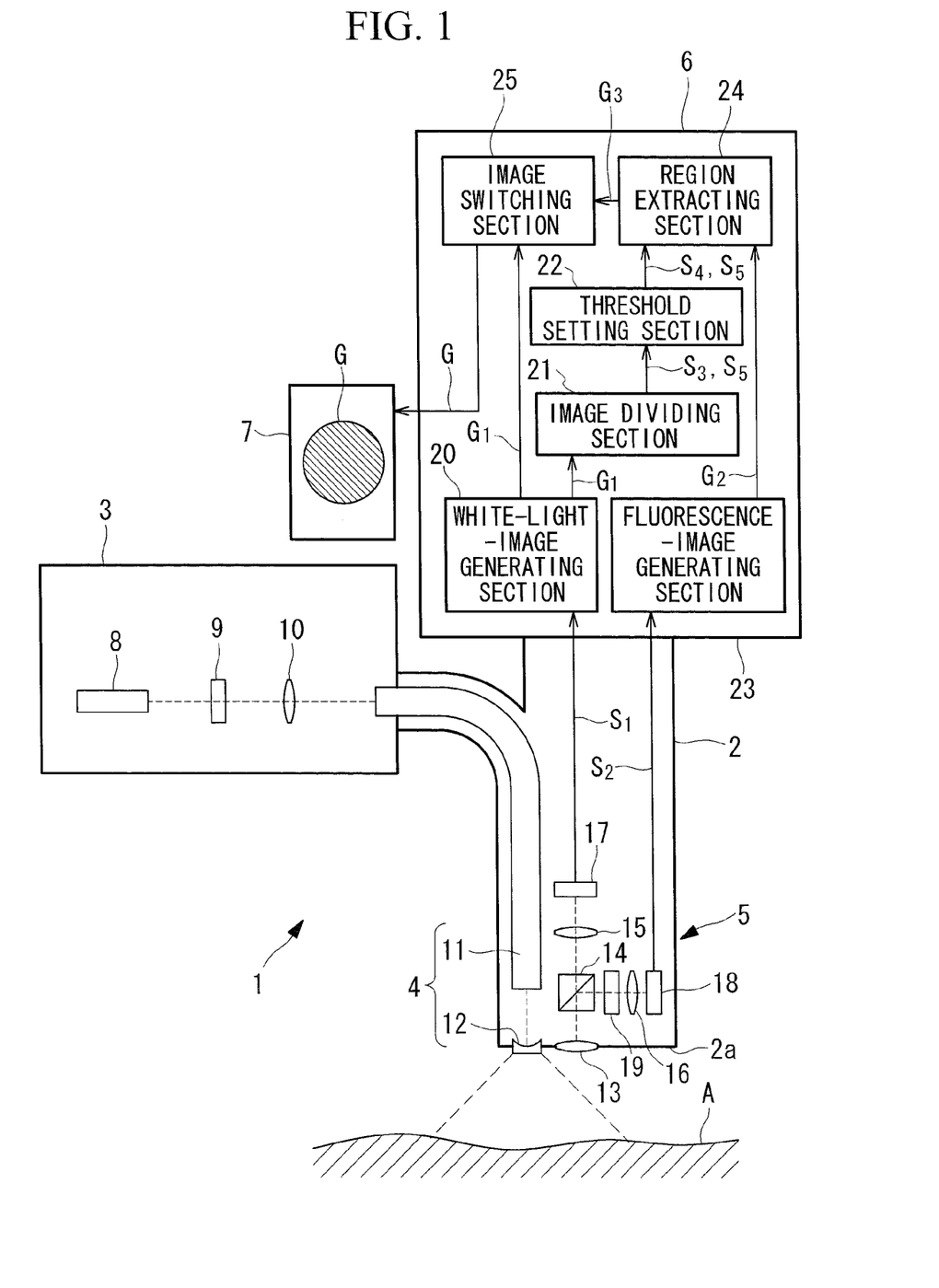
FIG. 1 is a diagram showing the overall configuration of a fluorescence observation device according to a first embodiment of the present invention.

A fluorescence observation device 1 according to this embodiment is an endoscope apparatus and is, as shown in FIG. 1, equipped with a long, thin inserted portion 2 to be inserted into a body, a light source (illuminating section) 3, an illumination unit (illuminating section) 4 that emits excitation light and illumination light from the light source 3 from the distal end of the inserted portion 2 toward a subject A, an image acquisition unit 5 which is provided at the distal end of the inserted portion 2 and which acquires image information of biological tissue serving as a subject A, an image processing unit 6 which is provided at the base end of the inserted portion 2 and which processes the image information acquired by the image acquisition unit 5, and a monitor 7 that displays an image G processed by the image processing unit 6.

The light source 3 is equipped with a xenon lamp 8, a filter 9 that extracts excitation light and illumination light (a wavelength band from 400 to 740 nm) from light emitted from the xenon lamp 8, and a coupling lens 10 that focuses the excitation light and the illumination light extracted by the filter 9.

The illumination unit 4 is equipped with a light guide fiber 11 which is disposed throughout substantially the entire length of the inserted portion 2 in the longitudinal direction and which guides the excitation light and the illumination light focused by the coupling lens 10 and an illumination optical system 12 which is provided at the distal end of the inserted portion 2 and which spreads out the excitation light and the illumination light guided by the light guide fiber 11 and radiates them onto the subject A facing a distal end face 2a of the inserted portion 2.

The image acquisition unit 5 is equipped with an objective lens 13 that collects light returning from a predetermined observation area of the subject A, a dichroic mirror 14 which reflects, of the light collected by the objective lens 13, light with an excitation wavelength or more (excitation light and fluorescence) and which allows white light (return light) with a wavelength shorter than the excitation wavelength to pass therethrough, two focusing lenses 15 and 16 that focus the white light which has passed through the dichroic mirror 14 and the fluorescence reflected by the dichroic mirror 14, respectively, and two image acquisition devices 17 and 18, such as CCDs, that acquire images of the white light and the fluorescence focused by the focusing lenses 15 and 16. In the drawing, reference sign 19 denotes an excitation-light cut filter that blocks excitation light in the light reflected by the dichroic mirror 14 (that allows, for example, only light with a wavelength band from 760 to 850 nm to pass therethrough).

The image processing unit 6 is equipped with a white-light-image generating section 20 that generates a white-light image $G_1$ from white-light image information $S_1$ acquired by the image acquisition device 17, an image separating section 21 that separates the white-light image $G_1$ into a plurality of separated regions R to obtain image separation information, a threshold setting section 22 that sets a threshold value $S_4$ for each of the separated regions R from the image separation information obtained by the image separating section 21, a fluorescence-image generating section 23 that generates a fluorescence image $G_2$ from fluorescence-image information $S_2$ acquired by the image acquisition device 18, a region extracting section 24 that extracts a high-luminance region from the fluorescence image $G_2$ on the basis of the threshold values $S_4$ for the individual regions set by the threshold setting section 22 to generate a high-luminance-region image $G_3$, and an image switching section 25 that switches between the high-luminance-region image $G_3$ generated by the region extracting section 24 and the white-light image $G_1$ and displays it on the monitor 7.

Figure 2:
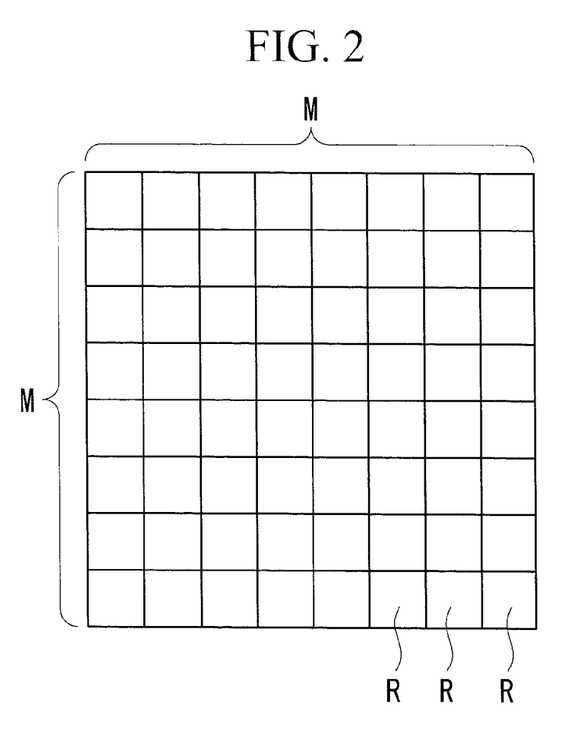
FIG. 2 is a diagram showing a plurality of separated regions in a square array with a preset number of separations.

The image separating section 21 separates the white-light image $G_1$ generated by the white-light-image generating section 20 in the form of a grid to generate the plurality of separated regions R that are arrayed vertically and horizontally. In this embodiment, as shown in FIG. 2, for example, the image separating section 21 generates the plurality of separated regions R in a square array with a preset number of separations (M×M).

Furthermore, the image separating section 21 stores region correspondence information showing the correspondence relationship between the positions of the individual separated regions R of the white-light image $G_1$ and the positions of small regions (not shown) of the fluorescence image $G_2$ in which an image of the subject A in the same area as the individual separated regions R is captured. Since the white-light image $G_1$ and the fluorescence image $G_2$ are obtained by separating the light returning from the same subject A with the dichroic mirror 14 and capturing an image thereof, as described above, the white-light image $G_1$ and the fluorescence image $G_2$ include an overlapped image-capture area, and the correspondence relationship between pixels in which an image of the same position of the subject A is captured is determined by the sizes and locations of the individual image acquisition devices 17 and 18. Accordingly, the region correspondence information is a correspondence table in which, for example, the address ranges of pixels that constitute the separated regions R of the white-light image $G_1$ and the address ranges $S_5$ of pixels that constitute the small regions of the fluorescence image $G_2$ are associated with each other.

The image separating section 21 outputs, for each of the small regions of the fluorescence image $G_2$, the address range $S_5$ of pixels in each small region and the gradation levels $S_3$ of a plurality of pixels that constitute the separated region R corresponding to the small region in association with each other by using the stored region correspondence information.

The threshold setting section 22 calculates an average gradation level by averaging, for each of the corresponding small regions, the gradation levels $S_3$ of the plurality of pixels that constitute each of the separated regions R input from the image separating section 21.

Furthermore, the threshold setting section 22 stores threshold values for extracting a high-luminance region of the fluorescence image $G_2$ as a function of the average gradation level.

Figure 3:
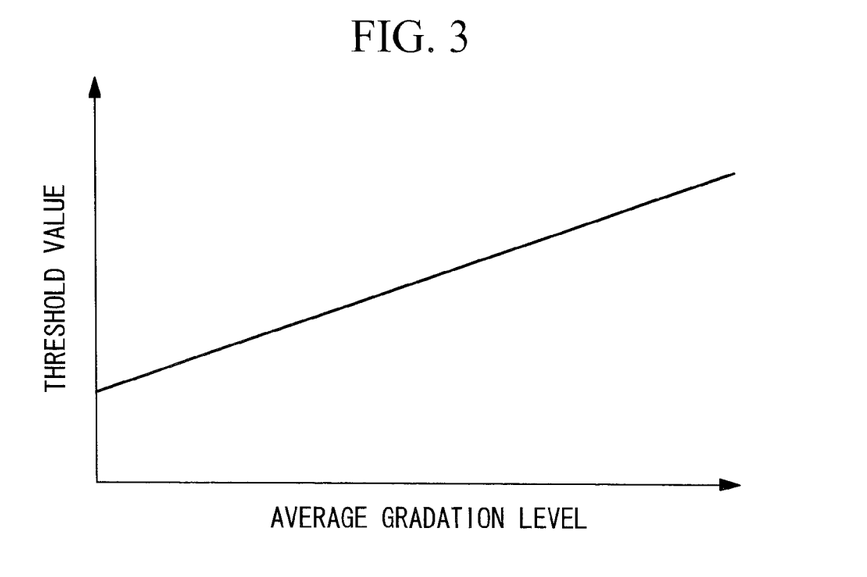
FIG. 3 is a diagram showing a graph of the relationship between an average gradation level and a threshold value, which is a monotonically increasing function that increases as the average gradation level increases.

This function is obtained in advance from the relationship between the average gradation level of the white-light image $G_1$ obtained by capturing an image of a standard sample or the like and a threshold value for accurately extracting a high-luminance region of the fluorescence image $G_2$. Since the fluorescence intensity tends to be high in a region in which the white-light image $G_1$ is bright, this function is a monotonically increasing function that increases as the average gradation level increases, as shown in FIG. 3.

The threshold setting section 22 obtains the threshold values $S_4$ by applying the average gradation levels calculated for the individual small regions to this function and outputs them in association with the address range $S_5$ of pixels that constitute each of the small regions.

The region extracting section 24 extracts a high-luminance region of the fluorescence image $G_2$ from the fluorescence image $G_2$ generated by the fluorescence-image generating section 23 by using the threshold values $S_4$ for the individual small regions received from the threshold setting section 22.

Specifically, the region extracting section 24 compares the gradation levels of the individual pixels of the fluorescence image $G_2$ and the threshold value $S_4$ set for the small region that the pixels belong to. As a result of the comparison, the region extracting section 24 extracts pixels whose gradation levels are higher than the threshold value $S_4$ as pixels that constitute a high-luminance region. By giving a value "1" to pixels whose gradation levels exceed the threshold value $S_4$ and giving a value "0" to pixels whose gradation levels are lower than or equal to the threshold value $S_4$, a set of pixels having value "1" is generated as the high-luminance-region image $G_3$.

The operation of the thus-configured fluorescence observation device 1 according to this embodiment will be described hereinbelow.

To observe biological tissue in a body, serving as the subject A, with the fluorescence observation device 1 according to this embodiment, the inserted portion 2 is inserted into the body to make the distal end face 2a of the inserted portion 2 face the subject A. The light source 3 is activated to generate excitation light and illumination light, and the excitation light and illumination light are introduced into the light guide fiber 11 through the coupling lens 10. The excitation light and the illumination light guided in the light guide fiber 11 and reaching the distal end of the inserted portion 2 are spread out by the illumination optical system 12 at the distal end of the inserted portion 2 to irradiate the subject A.

In the subject A, since a fluorescent substance contained therein is excited by the excitation light, fluorescence is generated, and white light is reflected at the surface of the subject A. The fluorescence and the reflected illumination light (white light) return from the subject A to the distal end face 2a of the inserted portion 2, and part of the fluorescence generated from within the observation area and the white light are collected by the objective lens 13.

The fluorescence and the white light collected by the objective lens 13 are separated according to their individual wavelengths by the dichroic mirror 14; for example, white light with a wavelength band from 400 to 700 nm is focused by the focusing lens 15 and is acquired as the white-light image information $S_1$ by the image acquisition device 17.

Furthermore, in the fluorescence and the white light collected by the objective lens 13, from the light reflected at the dichroic mirror 14, for example, light including excitation light and fluorescence in a wavelength band from 700 to 850 nm, the excitation light (for example, light at 740 nm or less) is removed by the excitation-light cut filter 19, and thereafter only the fluorescence is focused by the focusing lens 16 and is acquired as the fluorescence-image information $S_2$ by the image acquisition device 18.

The image information $S_1$ and $S_2$ acquired by the image acquisition devices 17 and 18, respectively, are sent to the image processing unit 6. In the image processing unit 6, the white-light image information $S_1$ is input to the white-light-image generating section 20 to generate the white-light image $G_1$. On the other hand, the fluorescence-image information $S_2$ is input to the fluorescence-image generating section 23 to generate the fluorescence image $G_2$.

The generated white-light image $G_1$ is separated into the M×M separated regions R in a square array by the image separating section 21. In the image separating section 21, the gradation levels $S_3$ of the plurality of pixels that constitute each of the separated regions R and the address range $S_5$ of the pixels in the small region of the fluorescence image $G_2$ corresponding to the separated region R are associated using the stored region correspondence information and are output to the threshold setting section 22.

In the threshold setting section 22, the gradation levels $S_3$ of the white-light image $G_1$ input from the image separating section 21 are averaged for each of the small regions to calculate an average gradation level. The calculated average gradation level is applied to the function stored in advance to calculate the threshold value $S_4$. Thus, the threshold value $S_4$ is set for each of the small regions of the fluorescence image $G_2$. The set threshold value $S_4$ is associated with the address range $S_5$ of pixels that constitute the small region and is output to the region extracting section 24.

In the region extracting section 24, the gradation level of each of the pixels of the fluorescence image $G_2$ generated by the fluorescence-image generating section 23 is compared with the threshold value $S_4$ input from the threshold setting section 22, and pixels having gradation levels exceeding the threshold value $S_4$ are extracted as a high-luminance region to generate the high-luminance-region image $G_3$.

The generated high-luminance-region image $G_3$ is switched to the white-light image $G_1$ by the image switching section 25, and the white-light image $G_1$ is displayed on the monitor 7. By the operator operating the image switching section 25 as necessary while observing the white-light image $G_1$ displayed on the monitor 7, the high-luminance-region image $G_3$ can be displayed on the monitor 7, and the high-luminance region of the fluorescence image $G_2$ can be observed in association with the white-light image $G_1$.

In this case, with the fluorescence observation device 1 according to this embodiment, the high-luminance region of the fluorescence image $G_2$ is extracted using the threshold values $S_4$ set for the individual small regions. Since the threshold values $S_4$ are set larger as the average gradation levels of the separated regions R of the white-light image $G_1$ corresponding to the small regions in the fluorescence image $G_2$ increase, it is possible to extract only a region of the subject A containing many fluorescent substances as a high-luminance region.

In other words, although a region with high gradation levels in the generated fluorescence image $G_2$ includes a region in which many fluorescent substances are contained in the subject A and a region strongly irradiated with excitation light, the region to be extracted as a lesion is only the region in which many fluorescent substances are contained in the subject A. Furthermore, the region of the white-light image $G_1$ with high gradation levels is a region irradiated with high-intensity white light due to the positional relationship between the illumination unit 4 and the subject A, so that the intensity of radiated excitation light is also high.

Accordingly, setting the threshold value $S_4$ high for the region of the white-light image $G_1$ with high gradation levels makes it difficult to extract, as a high-luminance region, a region of the fluorescence image $G_2$ with high gradation levels because it is irradiated with high-intensity excitation light.

As a result, a region in which many fluorescent substances are actually present can be extracted independently of the radiation distance and angle of the excitation light to the subject A. This has an advantage in that, for example, in the case where fluorescent substances that preferentially accumulate on a tumor produced in biological tissue are administered to perform observation, a region in which many fluorescent substances are actually present, that is, a tumor, can be accurately identified.

Furthermore, with the fluorescence observation device 1 according to this embodiment, since the threshold values $S_4$ for extracting a high-luminance region are set all at once for the individual separated regions R, the amount of calculations can be reduced as compared with a case in which the threshold values $S_4$ are set for individual pixels, thus allowing the time required for the calculation to be reduced.

Furthermore, since the influence of the light distribution is eliminated by using the gradation levels of the white-light image $G_1$, the amount of calculations can be reduced as compared with a case in which the influence of the light distribution is eliminated by dividing the fluorescence image $G_2$ by the white-light image $G_1$.

Figure 4:
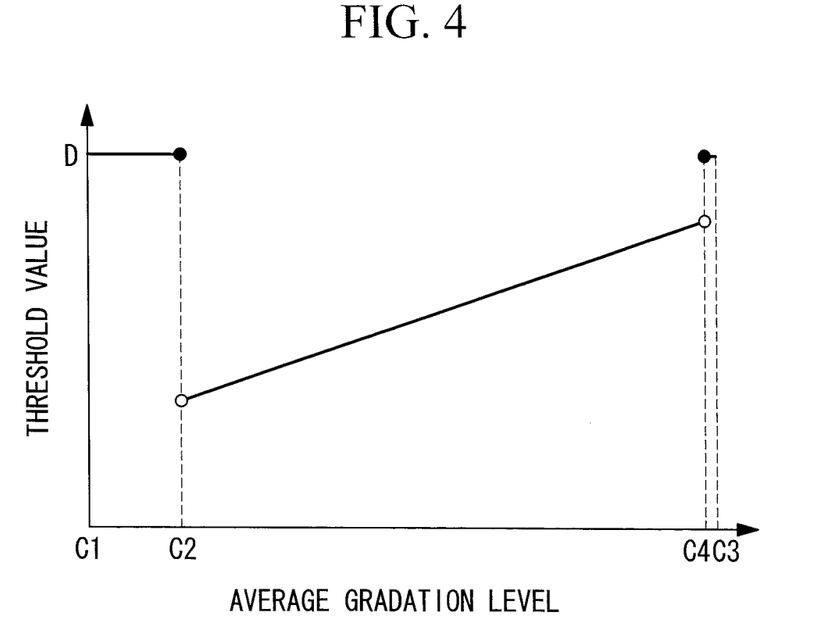
FIG. 4 is a diagram showing a graph of the relationship between the threshold value and the average gradation level when a function applied in accordance with the value of the average gradation level in FIG. 3 is changed.

In this embodiment, the threshold values $S_4$ are set by using the same function over the entire range of average gradation levels of the white-light image $G_1$; instead of this, however, the function to be applied may be changed depending on the average gradation level, as shown in FIG. 4.

For example, by using a first gradation level C2, which is slightly larger than a minimum gradation level C1 that the image acquisition device 17 that captures an image of the white-light image $G_1$ can take, and a second gradation level C4, which is slightly lower than a maximum gradation level C3, the above-described monotonically increasing function may be used between the first gradation level C2 and the second gradation level C4. In a range lower than the first gradation level C2 and a gradation level range higher than or equal to the second gradation level C4, preferably, a value D higher than the maximum gradation level that the image acquisition device 18 that captures an image of the fluorescence image $G_2$ can take is set as the threshold value $S_4$.

In the generated white-light image $G_1$, there is a high possibility that an area with low gradation levels contains much noise, and a region at the maximum gradation level is saturated. Therefore, it is difficult to select an appropriate threshold value $S_4$ for those regions, and thus, setting the threshold value $S_4$ large for those regions can prevent a region in which the reliability of the signal is low from being extracted as a high-luminance region.

Instead of setting the value D higher than the maximum gradation level, any threshold value $S_4$ larger than a value calculated using the function may be employed.

Furthermore, although this embodiment shows a linear function, as shown in FIG. 3, as an example of the function used, any other function may be employed instead, provided that it is a monotonically increasing function. Furthermore, a numerical expression may be stored as the function, or a map showing the correspondence relationship between the average gradation levels and the threshold values $S_4$ may be stored for setting the threshold value $S_4$.

Furthermore, although this embodiment is configured such that the threshold value $S_4$ is set from the average gradation level for each of the separated regions R constituted of a plurality of pixels, the threshold value $S_4$ may be set for each pixel. This allows a more detailed high-luminance region to be extracted.

Furthermore, in this embodiment, when the white-light image $G_1$ and the high-luminance region of the fluorescence image $G_2$ are to be displayed on the monitor 7 in association with the white-light image $G_1$ and be observed, they may be arranged side-by-side or may be overlapped.

Furthermore, although this embodiment is configured such that the image processing unit 6 is provided with the image separating section 21, it may be omitted. Accordingly, the threshold value $S_4$ may be set not for each of the separated regions R but for each pixel, to calculate a high-luminance region. This allows a high-luminance region to be accurately extracted.

Furthermore, in this embodiment, the high-luminance region may be extracted by obtaining the average gradation level of the small regions in the fluorescence image corresponding to the separated regions R and comparing this average gradation level with the threshold values $S_4$ of the separated regions R. This can reduce the amount of calculations for extracting the high-luminance region, allowing high-speed display.

Next, a fluorescence observation device 26 according to a second embodiment of the present invention will be described hereinbelow.

In the description of this embodiment, portions having common configurations with those of the fluorescence observation device 1 according to the first embodiment described above are given the same reference signs, and descriptions thereof will be omitted.

Figure 5:
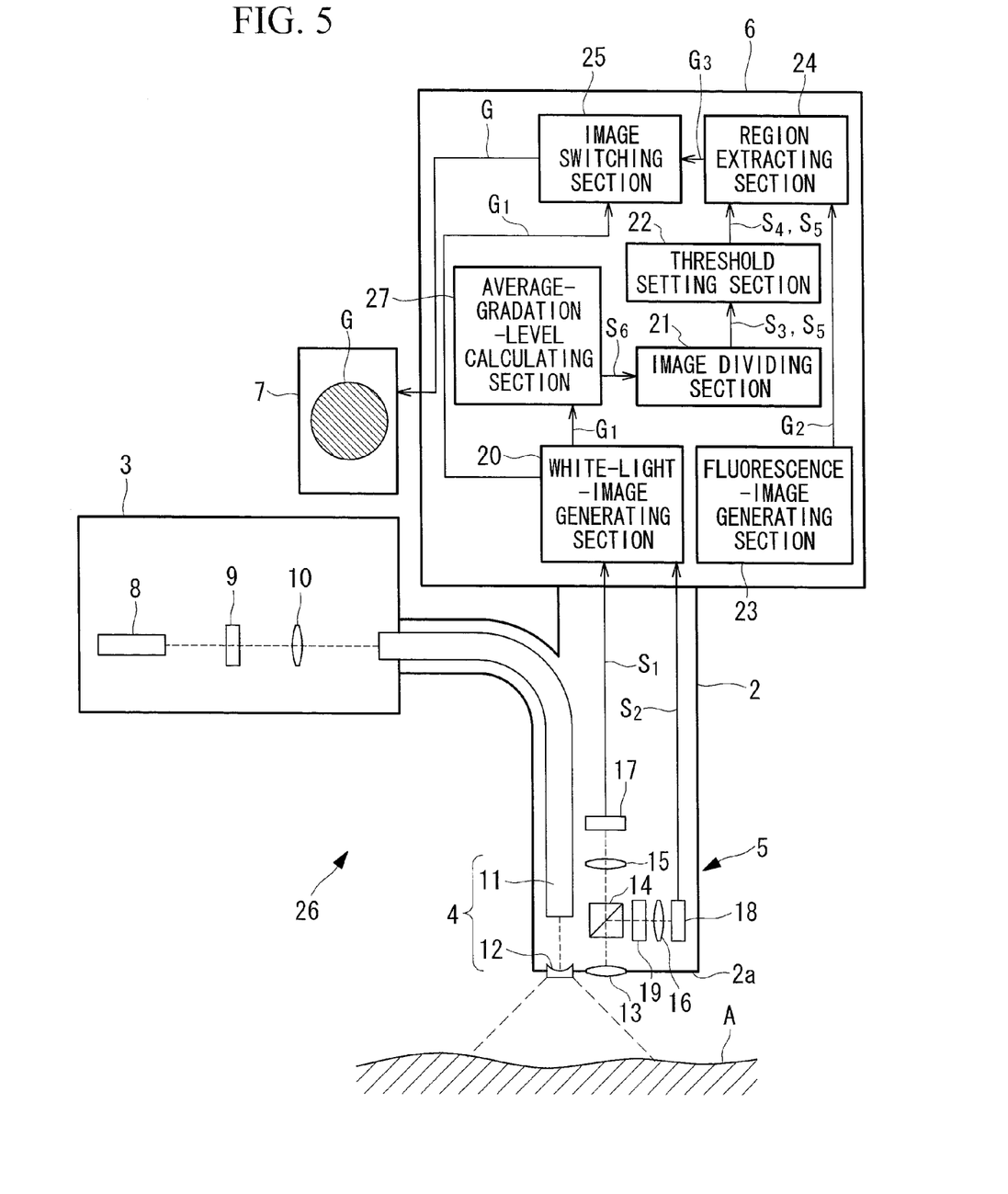
FIG. 5 is a diagram showing the overall configuration of a fluorescence observation device according to a second embodiment of the present invention.

As shown in FIG. 5, the fluorescence observation device 26 according to this embodiment is equipped with an average-gradation-level calculating section 27 between the white-light-image generating section 20 and the image separating section 21 of the image processing unit 6.

The average-gradation-level calculating section 27 calculates an average gradation level $S_6$ by averaging the gradation levels of all the pixels of the white-light image $G_1$ generated by the white-light-image generating section 20 and outputs it to the image separating section 21.

Furthermore, in this embodiment, the image separating section 21 stores correspondence information indicating the correspondence relationship between the pixels of the white-light image $G_1$ and the fluorescence image $G_2$, which are captured images of the same position of the subject A.

The image separating section 21 separates the image into a larger number of separations as the average gradation level $S_6$ increases, based on the average gradation level $S_6$ of the white-light image $G_1$ input from the average-gradation-level calculating section 27.

In other words, when the image separating section 21 sets the number of separations, the image separating section 21 determines the address ranges of pixels that constitute the individual separated regions R in the case where the white-light image $G_1$ is separated into the number of separations and determines the address ranges $S_5$ of the small regions of the fluorescence image $G_2$ corresponding to the address ranges of the separated regions R from the stored correspondence information. The image separating section 21 associates the gradation levels $S_3$ of the individual pixels that constitute the corresponding separated regions R with the determined address ranges $S_5$ of the individual small regions and outputs them.

The image separating section 21 separates the white-light image $G_1$ into the number of separations determined depending on the brightness of the average gradation level $S_6$ to generate the separated regions R.

The gradation levels $S_3$ of the plurality of pixels that constitute the separated regions R and the address ranges $S_5$ of the individual pixels that constitute the individual small regions of the fluorescence image $G_2$ corresponding to the separated regions R of the separated white-light image $G_1$ are associated with each other by using the stored correspondence information of the white-light image $G_1$ and the fluorescence image $G_2$ and are output.

With the thus-configured fluorescence observation device 26 according to this embodiment, when it is desired to observe the subject A in more detail, the subject A can be observed in more detail by bringing the illumination unit 4 and the subject A close to each other or making them face each other.

In this case, since the distance between the subject A and the illumination unit 4 is decreased, or the incident angle of the illumination light becomes steeper, the average gradation level $S_6$ of the white-light image $G_1$ increases. Accordingly, the high-luminance region can be extracted in detail for each of the separated regions R by increasing the number of separations of the white-light image $G_1$.

On the other hand, the subject A is roughly observed when the illumination unit 4 is separated from the subject A, or the incident angle becomes shallower, and thus, the average gradation level $S_6$ of the white-light image $G_1$ decreases. Accordingly, reducing the number of separations of the white-light image $G_1$ can reduce the number of calculations, thus allowing the time required for the calculation to be reduced.

Next, a fluorescence observation device 28 according to a third embodiment of the present invention will be described hereinbelow.

In the description of this embodiment, portions having common configurations with those of the fluorescence observation device 1 according to the first embodiment described above are given the same reference signs, and descriptions thereof will be omitted.

Figure 6:
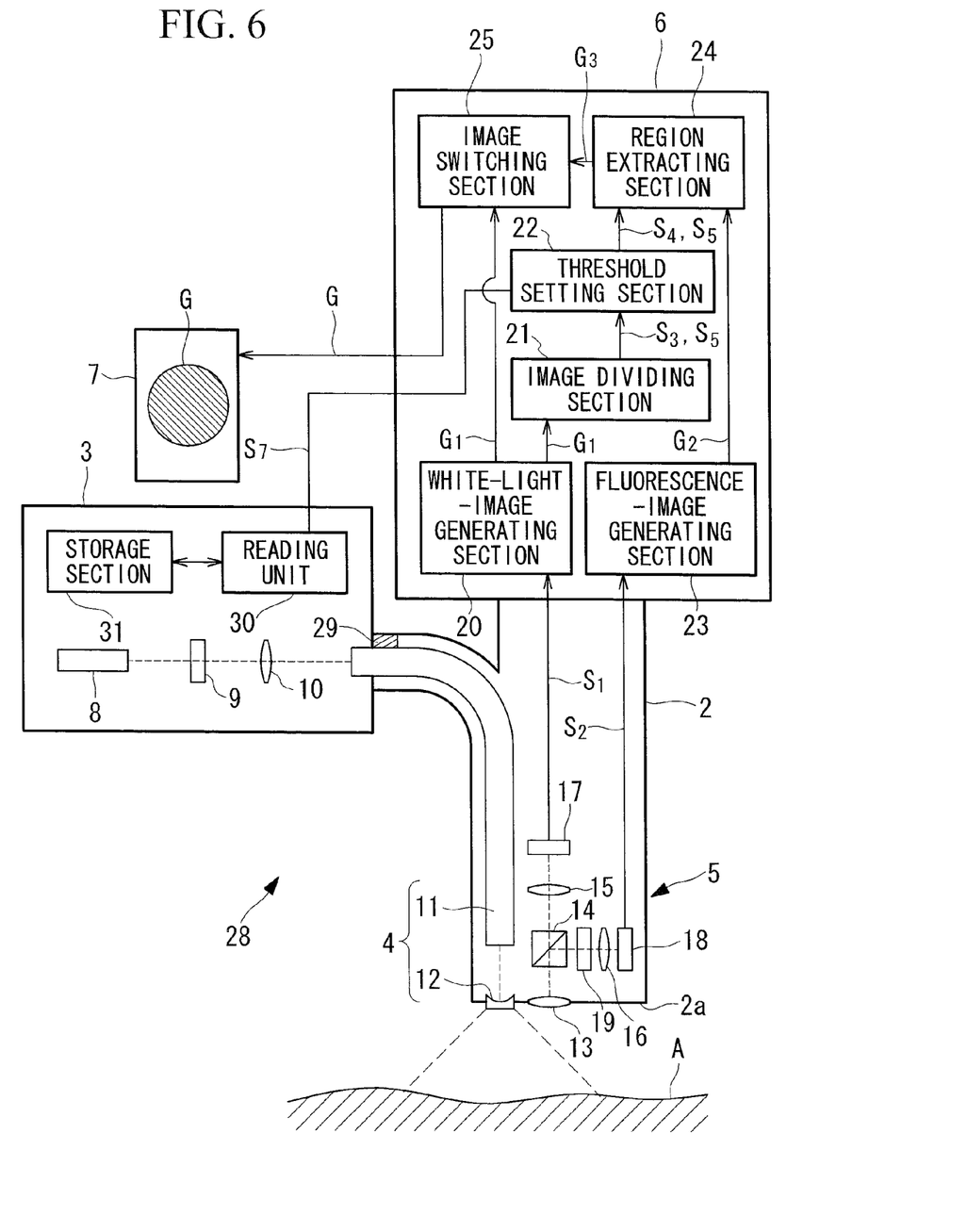
FIG. 6 is a diagram showing the overall configuration of a fluorescence observation device according to a third embodiment of the present invention.

As shown in FIG. 6, the fluorescence observation device 28 according to this embodiment is equipped with an inserted portion (detachable component) 2 that is detachable to and from the light source 3 and the image processing unit 6 so that it can be changed depending on the observation target site. The inserted portion 2 is provided with an IC chip 29 that stores identification information of the inserted portion 2.

Furthermore, the light source 3 to which the inserted portion 2 is attached is provided with a reading unit 30 that reads the identification information in the IC chip 29 and a storage section 31 that stores the identification information and a function $S_7$ in association with each other.

When the inserted portion 2 is attached, the reading unit 30 reads the identification information in the IC chip 29 provided at the inserted portion 2, acquires the function $S_7$ corresponding to the read identification information from the storage section 31, and outputs it to the threshold setting section 22.

Figure 7:
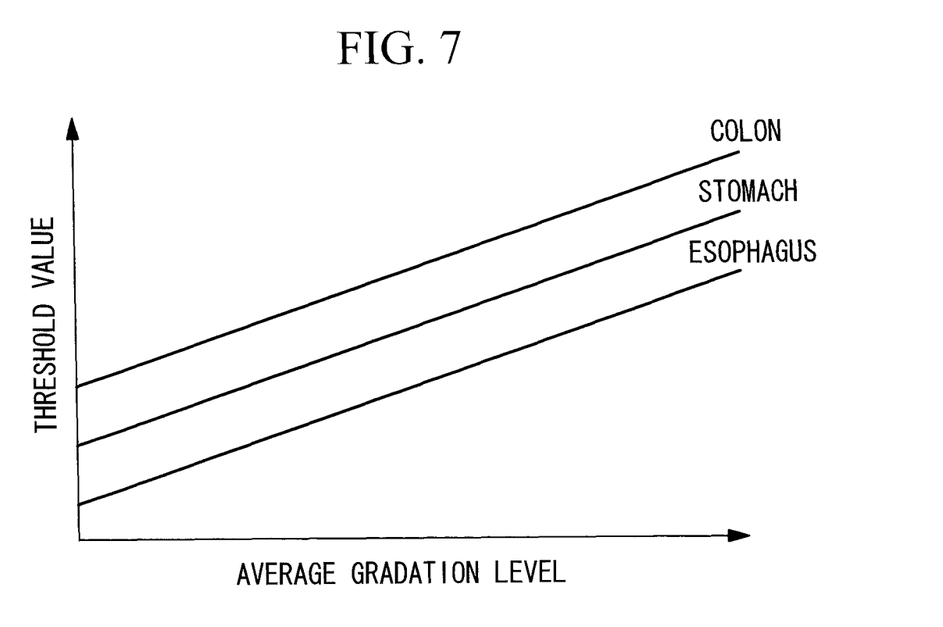
FIG. 7 is a diagram showing a graph that changes depending on the observation target site in FIG. 3.

Since the image acquisition units 5 of the individual inserted portions 2 have different optical characteristics so as to allow observation appropriate for individual observation target sites, when the individual inserted portions 2 are replaced with one another, the function $S_7$ for setting the threshold value $S_4$ from the gradation levels of the white-light image $G_1$ also changes depending on the observation target site, as shown in FIG. 7.

Thus, according to this embodiment, by reading the identification information stored in the IC chip 29 of the inserted portion 2, reading the function $S_7$ corresponding to the identification information from the storage section 31, and outputting it to the threshold setting section 22, the threshold setting section 22 can set the threshold value $S_4$ suitable for the observation target site.

In other words, an advantage is provided in that, even if the inserted portion 2 attached to the light source 3 is changed, the most suitable function $S_7$ for the inserted portion 2 can be set, so that a highly quantitative high-luminance region can be acquired.

In this embodiment, the light source 3 is equipped with the storage section 31, and the function $S_7$ is output to the threshold setting section 22; instead, functions associated with the identification information may be stored in the threshold setting section 22, and a corresponding function may be selected on the basis of identification information sent from the reading unit 30.

Furthermore, although the above individual embodiments have been described using endoscopes as an example of the fluorescence observation devices 1, 26, and 28, the present invention is not limited thereto; the present invention may be applied to any other fluorescence observation device.

Furthermore, although the above individual embodiments have been described using white light as an example of the reflected illumination light, the present invention is not limited thereto; any other light, such as the reflected excitation light and autofluorescence, may be used. Furthermore, the transmission wavelength regions of the dichroic mirror 14 and the excitation-light cut filter 19 are not limited to the ones described above; the present invention may be applied to any other wavelength.

The present invention offers the advantage that a region in which many fluorescent substances are present can be identified without carrying out a complicated calculation even if the fluorescence intensity has changed due to the distance and angle.

REFERENCE SIGNS LIST

A subject
$S_1$ white-light image information (return-light image)
$S_2$ fluorescence-image information (fluorescence image)
$S_4$ threshold value
1, 26, 28 fluorescence observation device
2 inserted portion (detachable component)
3 light source (illuminating section)
4 illumination unit (illuminating section)
17 image acquisition device (return-light-image capturing section)
18 image acquisition device (fluorescence-image capturing section)
21 image separating section
22 threshold setting section
24 region extracting section
27 average-gradation-level calculating section
30 reading unit (identification-information reading section)
31 storage section

The invention claimed is:

1. A fluorescence observation device comprising:
a light source that emits excitation light and illumination light onto a subject;
a fluorescence-image capturing sensor that acquires a fluorescence image by image-capturing fluorescence generated in the subject by irradiation with the excitation light from the light source;
a return-light-image capturing sensor that acquires a return-light image by image-capturing return light that returns from the subject by irradiation with the illumination light from the light source; and
a processor comprising hardware, the processor comprising:
a region extracting section that extracts a high-luminance region in which the fluorescence image acquired by the fluorescence-image capturing sensor has a gradation level higher than or equal to a set threshold value; and
a threshold setting section that sets the threshold value of the fluorescence image higher as the gradation level of the return-light image acquired by the return-light-image capturing sensor increases.

2. The fluorescence observation device according to claim 1, wherein, between a first gradation level and a second gradation level, the threshold setting section sets the threshold value according to a function that increases as the gradation level of the return-light image increases and, in a gradation level range lower than the first gradation level and in a gradation level range higher than the second gradation level, sets the threshold value larger than a value calculated using the function.

3. The fluorescence observation device according to claim 1, wherein
the threshold setting section sets the threshold value for each of separated regions formed by separating the return-light image at intervals of a plurality of pixels; and the region extracting section extracts the high-luminance region for individual small regions of the fluorescence image located at positions corresponding to the respective separated regions by using the threshold value set for each of the separated regions.

4. The fluorescence observation device according to claim 3, further comprising:
an image separating section that separates the return-light image at intervals of a plurality of pixels to form the separated regions and that associates the small regions of the fluorescence image located at positions corresponding to the respective separated regions with the individual separated regions; and
an average-gradation-level calculating section that calculates an average gradation level of a plurality of pixels in the return-light image,
wherein the image separating section increases the number of separations as the average gradation level calculated by the average-gradation-level calculating section increases.

5. The fluorescence observation device according to claim 1, comprising:
a detachable component that is attached and detached for changing observation conditions,
wherein identification information is stored in the detachable component;
an identification-information reading section that reads the identification information stored in the detachable component;
a storage section that stores the identification information, the gradation level of the return-light image, and the threshold value in association with one another; and
the threshold setting section that sets the threshold value stored in association by the storage section.

6. The fluorescence observation device according to claim 2, wherein
the threshold setting section sets the threshold value for each of separated regions formed by separating the return-light image at intervals of a plurality of pixels; and
the region extracting section extracts the high-luminance region for individual small regions of the fluorescence image located at positions corresponding to the respective separated regions by using the threshold value set for each of the separated regions.

7. The fluorescence observation device according to claim 6, further comprising:
an image separating section that separates the return-light image at intervals of a plurality of pixels to form the separated regions and that associates the small regions of the fluorescence image located at positions corresponding to the respective separated regions with the individual separated regions; and
an average-gradation-level calculating section that calculates an average gradation level of a plurality of pixels in the return-light image,
wherein the image separating section increases the number of separations as the average gradation level calculated by the average-gradation-level calculating section increases.

8. The fluorescence observation device according to claim 2, comprising:
a detachable component that is attached and detached for changing observation conditions,
wherein identification information is stored in the detachable component;
an identification-information reading section that reads the identification information stored in the detachable component;
a storage section that stores the identification information, the gradation level of the return-light image, and the threshold value in association with one another; and
the threshold setting section that sets the threshold value stored in association by the storage section.

9. The fluorescence observation device according to claim 3, comprising:
a detachable component that is attached and detached for changing observation conditions,
wherein identification information is stored in the detachable component;
an identification-information reading section that reads the identification information stored in the detachable component;
a storage section that stores the identification information, the gradation level of the return-light image, and the threshold value in association with one another; and
the threshold setting section that sets the threshold value stored in association by the storage section.

10. The fluorescence observation device according to claim 4, comprising:
a detachable component that is attached and detached for changing observation conditions,
wherein identification information is stored in the detachable component;
an identification-information reading section that reads the identification information stored in the detachable component;
a storage section that stores the identification information, the gradation level of the return-light image, and the threshold value in association with one another; and
the threshold setting section that sets the threshold value stored in association by the storage section.

11. The fluorescence observation device according to claim 6, comprising:
a detachable component that is attached and detached for changing observation conditions,
wherein identification information is stored in the detachable component;
an identification-information reading section that reads the identification information stored in the detachable component;
a storage section that stores the identification information, the gradation level of the return-light image, and the threshold value in association with one another; and
the threshold setting section that sets the threshold value stored in association by the storage section.

12. The fluorescence observation device according to claim 7, comprising:
a detachable component that is attached and detached for changing observation conditions,
wherein identification information is stored in the detachable component;
an identification-information reading section that reads the identification information stored in the detachable component;
a storage section that stores the identification information, the gradation level of the return-light image, and the threshold value in association with one another; and
the threshold setting section that sets the threshold value stored in association by the storage section.

* * * * *